US005494622A

United States Patent [19]
Heath et al.

[11] Patent Number: 5,494,622
[45] Date of Patent: Feb. 27, 1996

[54] APPARATUS AND METHOD FOR THE ZONED PLACEMENT OF SUPERABSORBENT MATERIAL

[75] Inventors: Mark G. Heath, Butte des Morts; John T. Hahn, Menasha; Lorry F. Sallee, Pine River; Joseph A. Mlinar, Appleton; Thomas M. Killian, Oneida; Thomas G. Olsen, Neenah, all of Wis.

[73] Assignee: Kimberly-Clark Corporation, Neenah, Wis.

[21] Appl. No.: 274,172

[22] Filed: Jul. 12, 1994

[51] Int. Cl.⁶ .............................. B27N 3/02; B27N 3/04; A61F 13/00
[52] U.S. Cl. .................... 264/40.1; 264/511; 264/517; 264/112; 264/113; 425/80.1; 425/81.1; 156/276
[58] Field of Search .................. 264/40.1, 510, 264/511, 517, 518, 112, 113; 425/81.1, 83.1, 80.1; 156/276

[56] References Cited

U.S. PATENT DOCUMENTS

| | | | |
|---|---|---|---|
| 2,331,271 | 10/1943 | Gilchrist | 128/284 |
| 2,897,109 | 7/1959 | Voigtman | 154/50 |
| 3,676,242 | 7/1972 | Prentice | 156/62.4 |
| 3,901,236 | 8/1975 | Assarsson et al. | 128/284 |
| 4,055,180 | 10/1977 | Karami | 128/287 |
| 4,055,181 | 10/1977 | Tritsch | 128/287 |
| 4,076,663 | 2/1978 | Masuda et al. | 260/17.4 GC |
| 4,224,366 | 9/1980 | McCabe, Jr. | 428/72 |
| 4,286,082 | 8/1981 | Tsubakimoto et al. | 526/240 |
| 4,327,728 | 5/1982 | Elias | 128/285 |
| 4,333,462 | 6/1982 | Holtman et al. | 128/287 |
| 4,360,021 | 11/1982 | Stima | 128/287 |
| 4,381,783 | 5/1983 | Elias | 604/368 |
| 4,413,996 | 11/1983 | Taylor | 604/382 |
| 4,414,255 | 11/1983 | Tokuyama et al. | 428/154 |
| 4,429,001 | 1/1984 | Kolpin et al. | 428/283 |
| 4,574,021 | 3/1986 | Endres et al. | 156/152 |
| 4,578,066 | 3/1986 | O'Connor | 604/366 |

(List continued on next page.)

FOREIGN PATENT DOCUMENTS

| | | |
|---|---|---|
| 1085102 | 9/1980 | Canada . |
| 1134126 | 10/1982 | Canada . |
| 1241504 | 9/1988 | Canada . |
| 1260249 | 9/1989 | Canada . |
| 0223487B1 | 5/1987 | European Pat. Off. . |
| 0222585 | 6/1987 | European Pat. Off. . |
| 0228353B1 | 7/1987 | European Pat. Off. . |
| 0339461B1 | 1/1993 | European Pat. Off. . |
| 2112828 | 7/1983 | United Kingdom . |
| 2113731 | 8/1983 | United Kingdom . |
| 2151272 | 7/1985 | United Kingdom . |
| WO89/01325 | 2/1989 | WIPO . |

OTHER PUBLICATIONS

Nonwovens World: A Journal for Management, Summer 1994, p. 13.

Primary Examiner—Mary Lynn Theisen
Attorney, Agent, or Firm—Paul Yee

[57] ABSTRACT

The present invention provides an apparatus and method for forming a composite web having selected discrete pocket regions which are distributed on a carrier layer and contain high-absorbency material. The invention includes a pattern chamber having opposed side walls, an entrance end wall and an exit end wall. A particulate supplying mechanism provides particles of high-absorbency material into the pattern chamber, and a web supplying mechanism provides a gas permeable carrier layer. A foraminous forming mechanism moves the carrier layer through the pattern chamber, and the forming mechanism includes a pattern of openings which are formed therethrough and are arranged to provide for a selected pattern of the discrete pocket regions. A vacuum supplying mechanism provides a selected level of relatively low gas pressure at an underside region of the forming mechanism to produce a selected gas-flow through the carrier layer and the foraminous forming mechanism to form the pocket regions. A covering mechanism provides a layer of liquid-permeable covering material to sandwich said pocket regions of high-absorbency material between said carrier layer and said covering layer.

22 Claims, 11 Drawing Sheets

U.S. PATENT DOCUMENTS

| | | | |
|---|---|---|---|
| 4,592,751 | 6/1986 | Gegelys | 604/368 |
| 4,604,313 | 8/1986 | McFarland et al. | 428/172 |
| 4,610,678 | 9/1986 | Weisman et al. | 604/368 |
| 4,655,757 | 4/1987 | McFarland et al. | 604/366 |
| 4,666,647 | 5/1987 | Enloe et al. | 264/121 |
| 4,670,011 | 6/1987 | Mesek | 604/378 |
| 4,676,785 | 6/1987 | Battista | 604/369 |
| 4,715,918 | 12/1987 | Lang | 156/273.1 |
| 4,724,114 | 2/1988 | McFarland et al. | 264/510 |
| 4,741,941 | 5/1988 | Englebert et al. | 428/71 |
| 4,761,258 | 8/1988 | Enloe | 264/518 |
| 4,840,692 | 6/1989 | Kamstrup-Larsen | 156/252 |
| 4,886,509 | 12/1989 | Mattsson | 604/349 |
| 4,892,535 | 1/1990 | Bjornberg et al. | 604/380 |
| 4,908,175 | 3/1990 | Angstadt | 264/113 |
| 4,949,668 | 8/1990 | Heindel et al. | 118/314 |
| 4,960,477 | 10/1990 | Mesek | 156/209 |
| 4,988,344 | 1/1991 | Reising et al. | 604/368 |
| 4,994,053 | 2/1991 | Lang | 604/367 |
| 5,017,324 | 5/1991 | Kaiser et al. | 264/510 |
| 5,028,224 | 7/1991 | Pieper et al. | 425/80.1 |
| 5,030,314 | 7/1991 | Lang | 156/390 |
| 5,072,687 | 12/1991 | Mitchell et al. | 118/37 |
| 5,118,376 | 6/1992 | Pigneul et al. | 156/219 |
| 5,149,335 | 9/1992 | Kellenberger et al. | 604/372 |
| 5,175,046 | 12/1992 | Nguyen | 428/198 |
| 5,196,470 | 3/1993 | Anderson et al. | 524/379 |
| 5,213,817 | 5/1993 | Pelley | 425/81.1 |
| 5,411,497 | 5/1995 | Tanzer et al. | 604/368 |
| 5,425,725 | 6/1995 | Tanzer et al. | 604/368 |
| 5,429,788 | 7/1995 | Ribble et al. | 264/510 |

APPARATUS AND METHOD FOR THE ZONED PLACEMENT OF SUPERABSORBENT MATERIAL

FIELD OF THE INVENTION

The present invention relates to an apparatus and method for the selective placement of particulate material on a substrate. More particularly, the present invention relates to a technique for the selective zoned placement of particulate material into discrete pocket regions of a moving substrate.

BACKGROUND OF THE INVENTION

Various techniques have been employed to air lay fibrous cellulosic material to form a fibrous web that can be employed to produce an absorbent pad for an absorbent article, such as a disposable diaper or the like. Other techniques have been employed to air lay mixtures of hydrophilic cellulosic fibers and superabsorbent particles. For example, see U.S. Pat. No. 4,610,678 entitled HIGH-DENSITY ABSORBENT STRUCTURES and issued Sep. 9, 1986 to Weisman et al.

Particular techniques have been employed to form selected regions of superabsorbent material intermittently located along the length of a web of absorbent fibers. For example, see U.S. Pat. No. 5,028,224 entitled METHOD AND APPARATUS FOR INTERMITTENTLY DEPOSITING PARTICULATE MATERIAL IN A SUBSTRATE AND ARTICLE MADE THEREWITH, issued Jul. 2, 1991 to C. Pieper et al. (Docket No. 8761). Also, see U.S. Pat. No. 5,017,324 issued May 21, 1991 to Kaiser et al.

Absorbent structures have also been provided with discrete separated regions or pockets of superabsorbent material. Examples of such structures are described in U.S. Pat. No. 4,055,181 issued Oct. 25, 1977, to H. Karami; U.S. Pat. No. 4,360,021 issued Nov. 23, 1982, to J. Stima and U.S. Pat. No. 4,715,918 issued to Lang.

Conventional techniques, such as those described above, have not provided an adequate mechanism for producing discrete pockets of particulate, high absorbency material on a moving carrier web at desired high rates of manufacture. The techniques have not been able to operate at sufficiently high speeds, and have not been sufficiently able to reliably produce desired arrays composed of pocket regions arranged in predetermined patterns.

BRIEF DESCRIPTION OF THE INVENTION

Generally stated, the present invention provides an apparatus for forming a composite web having selected discrete pocket regions which are distributed on a carrier layer and contain high-absorbency material. The apparatus includes a pattern chamber having opposed side walls, an entrance end wall and an exit end wall. A particulate supplying means provides particles of high-absorbency material into the pattern chamber, and a web supplying means provides a gas permeable carrier layer. A foraminous forming means moves the carrier layer through the pattern chamber, and the forming means includes a pattern of openings which are formed therethrough and are arranged to provide for a selected pattern of the discrete pocket regions. A vacuum supplying means provides a selected level of relatively low gas pressure at an underside region of the forming means to produce a selected gas-flow through the carrier layer and the foraminous forming means. A covering means provides a layer of liquid-permeable covering material to sandwich said pocket regions of high-absorbency material between said carrier layer and said covering layer.

The invention also provides a method for forming a composite web having selected discrete pocket regions which are distributed on a carrier layer and contain high-absorbency material. The method includes the steps of providing articles of high-absorbency material into a pattern chamber and providing a gas permeable carrier layer. The carrier layer is moved through the pattern chamber with a foraminous forming means having a pattern of openings which are formed therethrough and are arranged to provide for a selected pattern of the discrete pocket regions. A selected level of relatively low gas pressure is supplied on an underside region of the forming means to produce a selected airflow through the carrier layer and the foraminous forming means. A layer of liquid-permeable covering material is provided to sandwich said pocket regions of high-absorbency material between said carrier layer and said covering layer.

In other aspects of the invention, the high-absorbency material can substantially cleared from intermediate sections of the carrier layer, which are located between the selected pocket regions, by a sweeping means. In addition aspects, particular configurations of the invention can be arranged to deliver a selected quantity of fibrous matrix material into the pattern chamber. Other aspects of the invention can be configured to hold the discrete pocket regions of high-absorbency material on the carrier layer after the forming means has moved the carrier layer out of the pattern chamber. Particular aspects of the invention can be constructed to regulate a tension applied to the carrier layer to control a porosity of the carrier layer within the pattern chamber. Further aspects of the invention are described herein below.

The distinctive apparatus and method of the invention can reliably produce desired pattern arrays of multiple, individual pockets of high-absorbency material. The patterned pocket arrays can be more efficiently and more uniformly produced at high speed. In addition, the invention can provide improved securement and retention of the high-absorbency material within the appointed pocket regions.

As a result, when compared to conventional techniques, the various aspects of the present invention can provide an improved technique for manufacturing a composite, highly absorbent web which can provide a more efficient utilization of the high-absorbency material contained in the segregated pocket regions.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

For the purposes of the present description, the invention will be described in the context of producing an absorbent structure for a disposable diaper. It should be readily appreciated, however, that the present invention can be configured and employed to produce absorbent structures which can be incorporated into various types of other absorbent articles, such as feminine care products, incontinence garments, child care products, absorbent pads and the like.

Figure 1:
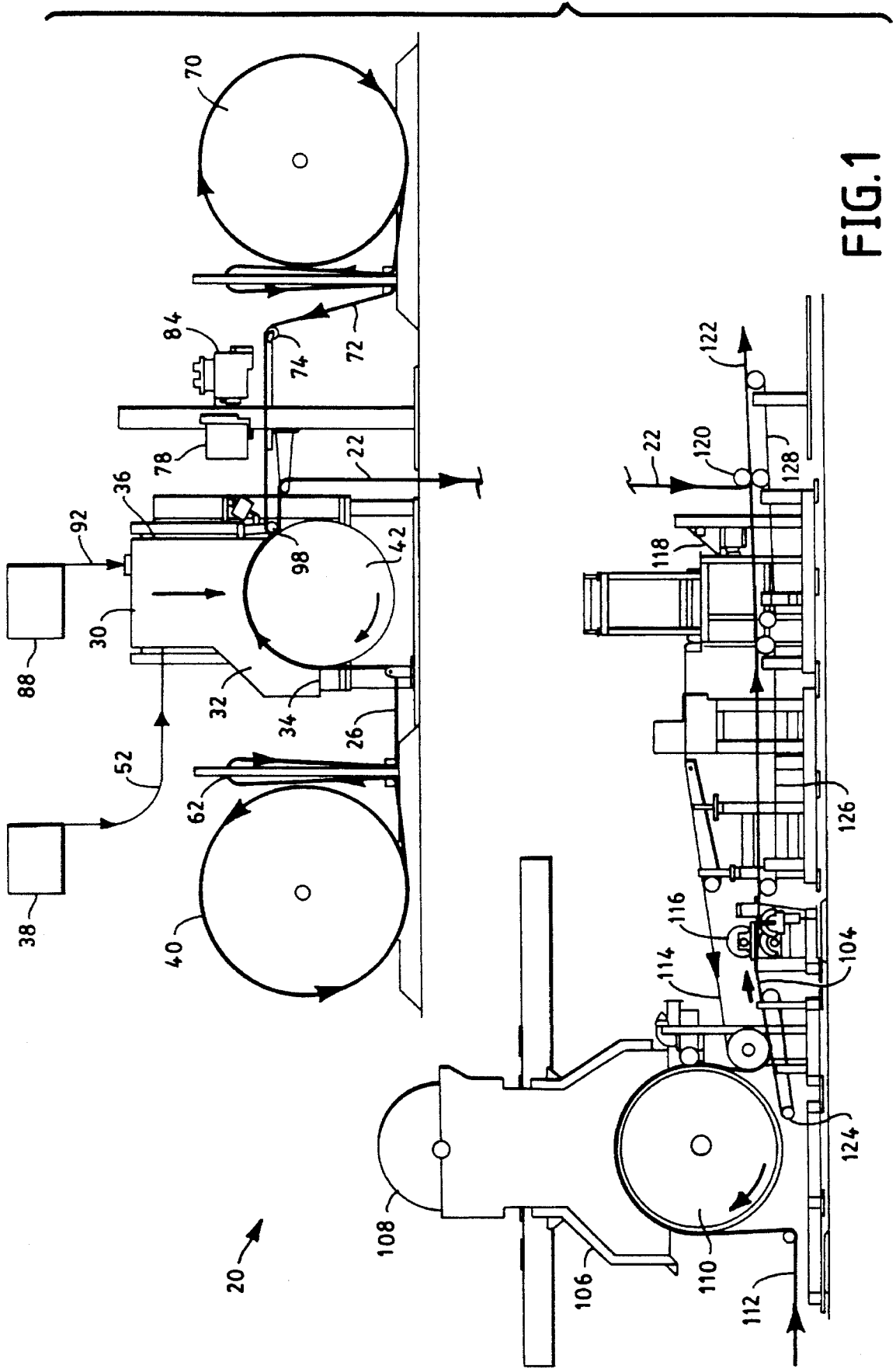
FIG. 1 representatively shows a schematic diagram of a representative method and apparatus of the invention.
Figure 2:
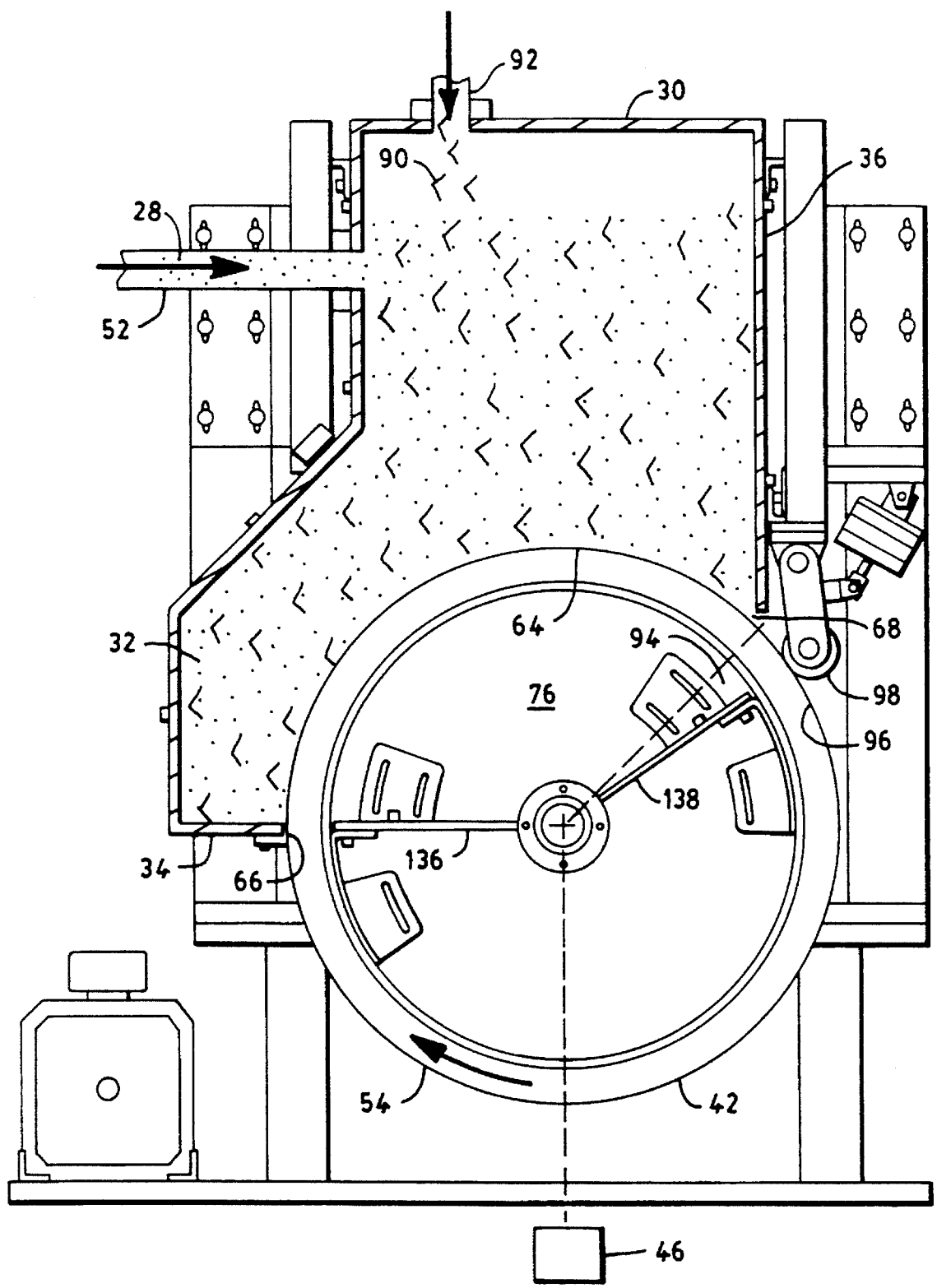
FIG. 2 representatively shows a pattern chamber and forming drum employed with the present invention.
Figure 8:
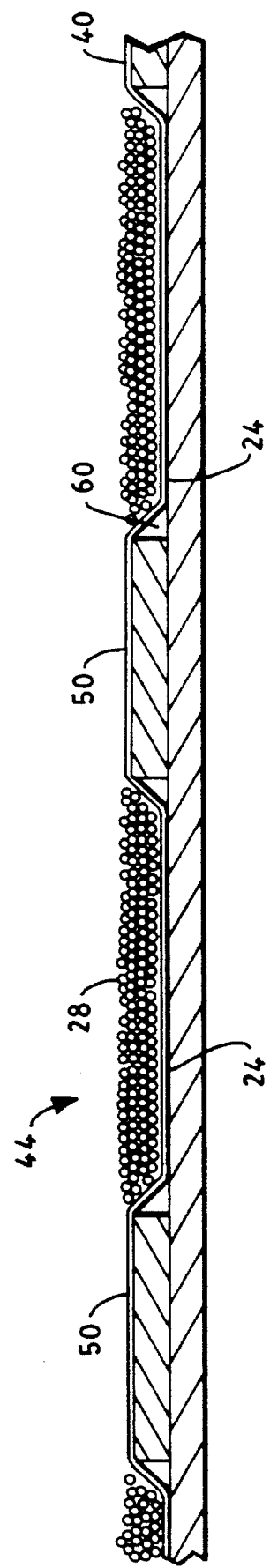
FIG. 8 representatively shows a cross-sectional view of a carrier layer which has been drawn onto a foraminous forming surface and includes pocket regions of superabsorbent material airlaid thereon.

With reference to FIGS. 1 and 2, the present invention can provide an apparatus, shown generally at 20, for forming a composite web 22 having a selected plurality of discrete pocket regions which are distributed on a carrier layer 26 and contain a selected quantity of high-absorbency material 28. The representatively shown apparatus includes a pattern chamber 30, and a particulate supplying means 38 for providing particles of high-absorbency material 28 into pattern chamber 30. A web supplying means 40 provides a gas permeable carrier layer 26, and a foraminous forming means 42 moves the carrier layer 26 through pattern chamber 30. The forming means includes a pattern of openings 44 which are formed therethrough and are arranged to provide for a selected pattern of the discrete pocket regions 24 (FIG. 8). A vacuum supplying means 46 provides a selected level of relatively low gas pressure within a primary vacuum chamber 76 located on an underside region of the forming means 42 to produce a selected gas flow through the carrier layer 26 and the foraminous forming means. The resultant gas flow operably directs the high-absorbency material to form the pattern of substantially discrete, and substantially spaced-apart pocket regions. A covering means, such as a mechanism comprising assembly roller 98, provides a layer of liquid-permeable covering material, such as a fibrous web 72, to sandwich said pocket regions of high-absorbency material between said carrier layer and the covering layer.

With reference to FIG. 2, pattern chamber 30 includes a pair of laterally opposed side walls 32, an entrance end wall 34 and an exit end wall 36. The pattern chamber is suitably constructed and arranged to operably direct a selected flow of high-absorbency material onto a foraminous forming means, such as provided by rotatable forming drum 42. It should be appreciated that other particulate or fibrous materials may also be introduced into pattern chamber 30, as desired. A particulate supplying means, such as a K-Tron weight and loss feeder, Model No. K10s, type of particle delivery system, and be configured to deliver required amounts of high-absorbency material 28 through an appropriate supply conduit 52 into pattern chamber 30. In particular arrangements, a conventional air-conveying system may be employed to move the high-absorbency material through the conduit 52. Alternatively, the high-absorbency material can, for example, be operably metered and substantially gravity-fed from the K-Tron delivery system into the pattern chamber 30. In such a configuration the delivery system can be mounted in close proximity to the top section of the pattern chamber, and can deliver the high-absorbency material directly into the pattern chamber without introducing additional conveying air.

The high-absorbency material can comprise absorbent gelling materials, such as superabsorbents. The absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable.

Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrol idone), poly(vinylmorphol inone), poly(vinyl alcohol ), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

Suitable high-absorbency materials can have particular characteristics of Absorbent Capacity (sometimes referred to as "AC"), Deformation Under Load (sometimes referred to as "DUL"), and the Wicking Index (sometimes referred to as "WI"). These parameters are described in detail in U.S. patent application Ser. No. 757,787 of S. Byerly et al. and entitled "ABSORBENT COMPOSITES AND ABSORBENT ARTICLES CONTAINING SAME" (Attorney Docket No. 0174), which was filed on Sep. 11, 1991 and is hereby incorporated by reference in a manner that is consistent (not in contradiction) with the present specification.

In the illustrated embodiment, for example, the high-absorbency material may be composed of a partial sodium salt of a cross-linked polyacrylate/polyalcohol copolymer, such as FAVOR SAB 870 superabsorbent polymer which is available from Stockhausen, Inc., a company having offices located in Greensboro, North Carolina.

The web supplying means, such as provided by web supply roll 40, can include a conventional spindle and supply roll controlling mechanism of the type that is well known in the art. For example, suitable spindle and control mechanisms are available from Martin Automatic Inc., a company having offices located in Rockford, Illinois.

The gas permeable carrier layer 26 provided by web supply roll 40 can be any porous, gas permeable web material which has sufficient strength to process through the apparatus and is sufficiently porous to permit adequate gas flow therethrough. The permitted gas flow should be at a rate which is adequate to carry and direct the particles of high-absorbency material 28 onto the appointed pocket regions of the carrier layer. The carrier layer may, for example, comprise a porous film or fibrous layer. The fibrous layer may comprise a fibrous tissue, a woven or nonwoven fabric, a cellulosic fibrous web, or the like. In the illustrated embodiment, for example, carrier layer 26 can comprise a cellulosic tissue composed of a conventional forming tissue having a basis weight of about 16.6 gsm and manufactured by a continuous wet press (CWP) process from a furnish composed of 100% LL-19 Northern Softwood Kraft (NSWK) fiber. The LL-19 fiber was obtained from Kimberly-Clark Forest Products, Inc., Terrace Bay, Ontario, Canada. The forming tissue has a Frazier Porosity of about 50–350 cfm/ft$^2$ (cubic-feet-per-minute per square foot).

The illustrated embodiment of the foraminous forming means includes a rotatable forming drum 42. In alternative configurations of the invention, the foraminous forming means may comprise a substantially endless, movable forming belt carried upon a system of transporting rollers. Typical forming drum mechanisms and forming surface constructions are, for example, described in U.S. Pat. No. 4,666,647 issued May 19, 1987 to K. Enloe et al. (Attorney Docket No. 6900) and U.S. Pat. No. 4,761,258 issued Aug. 2, 1988 to K. Enloe (Attorney Docket No. 6999), the disclosures of which are hereby incorporated by reference in a manner that is consistent herewith. Suitable forming belt systems are available from Paper Converting Machine Company, a business having offices located in Green Bay, Wisconsin.

An operable driving means, such as a conventional electric motor or the like, is constructed and arranged to rotate or otherwise move and translate an appointed forming surface of the foraminous forming means, such as an outer peripheral surface 54 of forming drum 42, at a predetermined surface speed along a desired manufacturing direction, as indicated. The various configurations of the invention can advantageously provide desired pocket structures while operating at high surface speeds of at least about 1 m/sec. Alternatively, the surface speed can be at least about 2 m/sec, and optionally, can be at least about 3 m/sec to provide improved performance. In other aspects of the invention, the speed of the forming surface can be not more than about 7 m/sec. Alternatively, the surface speed can be not more than about 6 m/sec, and optionally can be not more than about 5 m/sec to provide desired benefits. Since the present invention can reliably generate the discrete pocket structures while operating at the high speeds, the various configurations of the invention can more efficiently operate at lower cost.

Carrier layer 26 is operably delivered onto the outer peripheral surface of the forming drum 42. As the forming drum rotates, the moving surface of the forming drum transports the carrier layer into, through, and then out from the pattern chamber 30.

Figure 3:
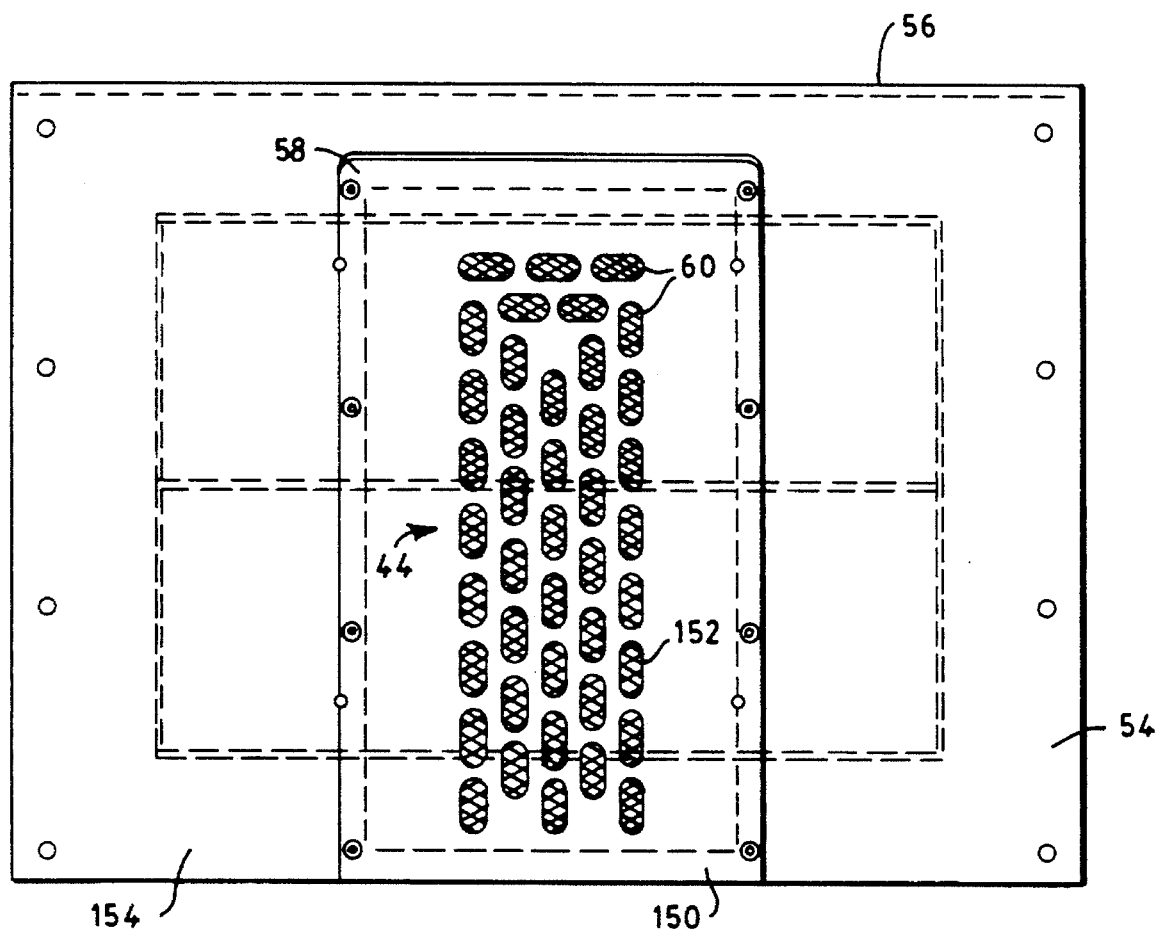
FIG. 3 representatively shows a top plan view of a forming screen segment which can be located on the forming drum and employed to form a desired pattern of pocket regions.

With reference to FIG. 3, the peripheral drum surface 54 can be operationally divided into a series of predetermined individual article segments 56. Each article segment generally corresponds to a section of the composite web 26 which is appointed for placement on a single absorbent article. The peripheral drum surface 54 can further comprise a plurality of screen segments 58 which are serially positioned and longitudinally spaced along the drum circumference.

Figure 4:
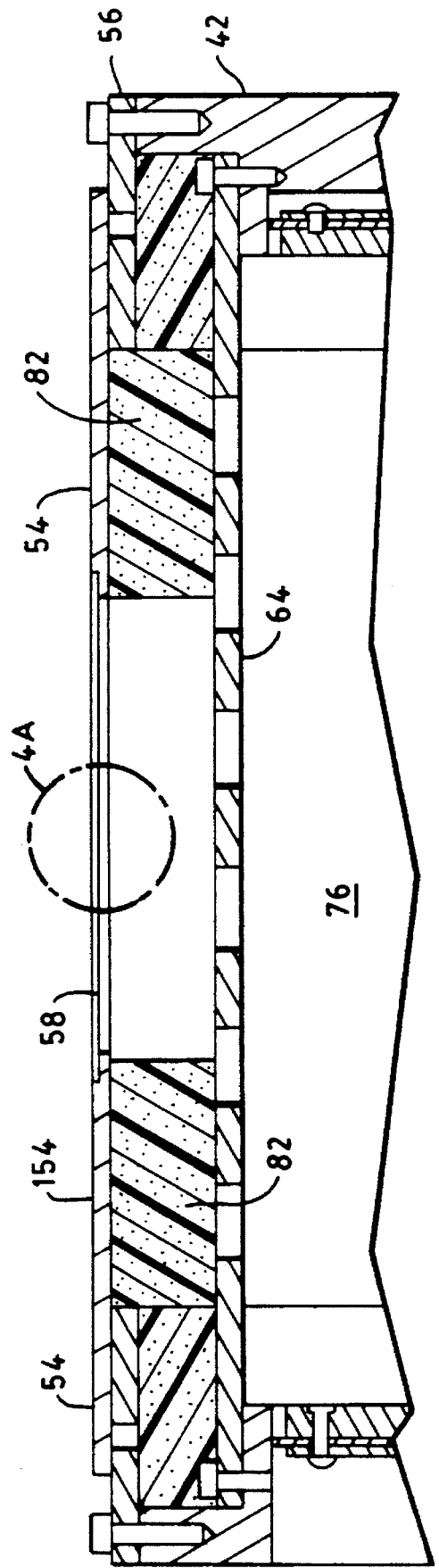
FIG. 4 representatively shows a cross-sectional view of a peripheral portion of the forming drum taken through a screen segment.
Figure 4A:
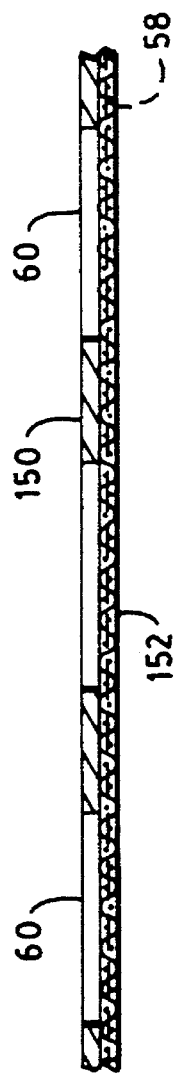
FIG. 4A representatively shows an enlarged, cross-sectional view of a portion of the forming screen segment illustrated in FIG. 4.

With reference to FIG. 4 and 4A, each of the screen segments 58 comprises a pattern plate 150 and a pattern screen 152, and each screen segment can be mounted for support in a frame 154.

Figure 4B:
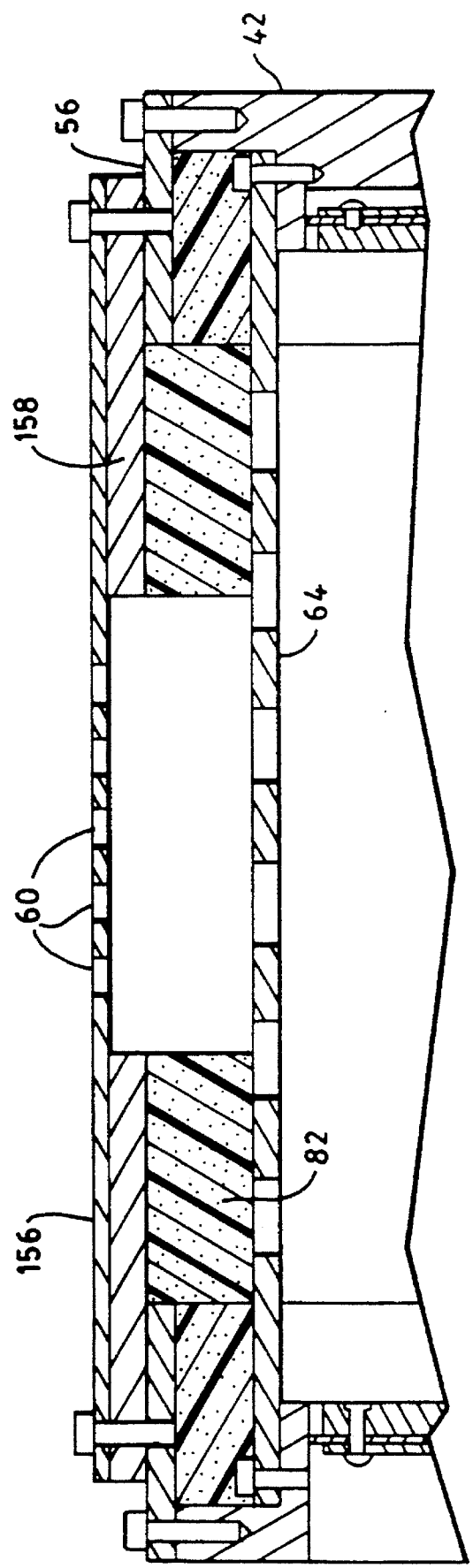
FIG. 4B representatively shows a cross-sectional view of a peripheral portion of the forming drum taken through an alternative article segment composed of a shell section and support insert.
Figure 5:
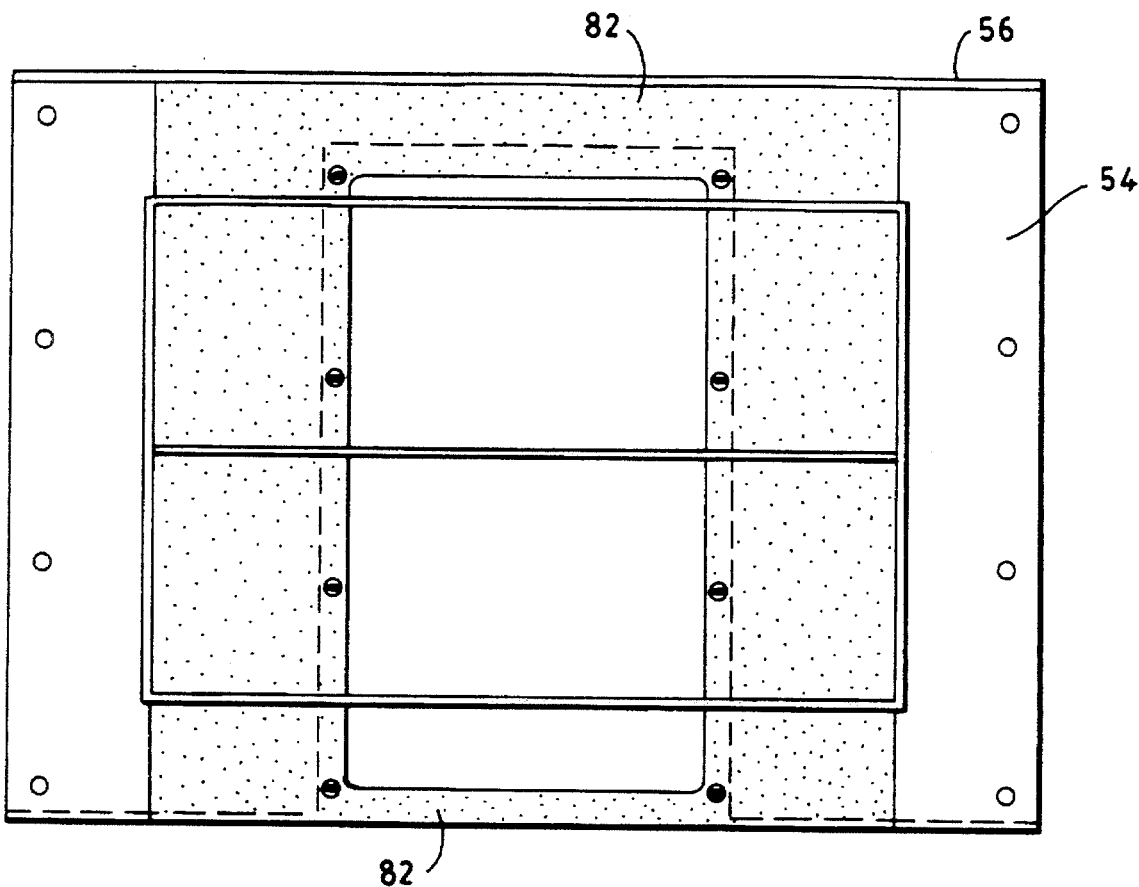
FIG. 5 representatively shows a bottom view of an article segment of the forming drum in which the forming screen and associated covering plates have been removed.
Figure 6:
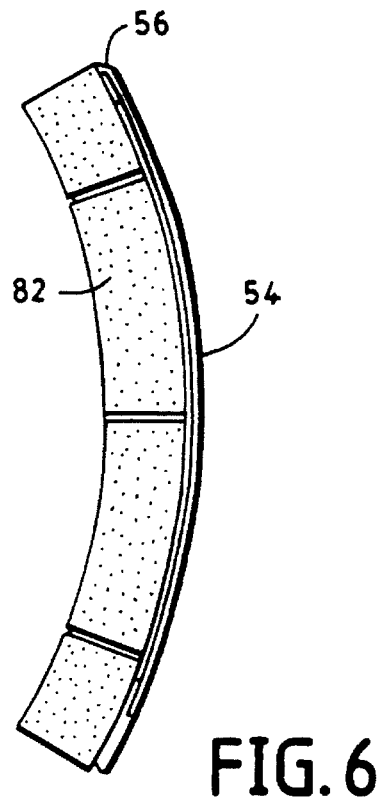
FIG. 6 representatively shows a cross-sectional, side view of an article segment of the forming drum.

With reference to FIG. 4B, each article segment 56 of the peripheral drum surface 54 can alternatively be provided by a rolled shell section 156. Accordingly, the drum peripheral surface would comprise a plurality of the shell sections. The shell sections 156 are constructed of a material, such as metal, that is sufficiently strong to withstand the forces and stresses encountered during operation. The desired pattern array of openings 60 are formed through the thickness dimension of each of the shell sections, and in the representatively shown embodiment, a support insert 158 is operably mounted subjacent and against the inside surface of each shell section. The support insert connects to the forming drum structure with suitable fastener, such as the illustrated bolts, and the radial thickness of the insert 158 can be selected to control the operational diameter and rotational speed of the forming drum. The support insert extends around the perimeter of the area occupied by the pattern array of openings 60, and includes a large opening therethrough which allows the passage of gas flow through the pattern openings and into the interior of the forming drum. With this configuration, the pattern screens 152 may be eliminated.

Each screen segment 58 includes a predetermined pattern of openings formed therethrough. The resultant pattern array 44 is suitably constructed and arranged to provide for the desired pattern of discrete pocket regions 24 formed onto carrier layer 26.

Figure 7:
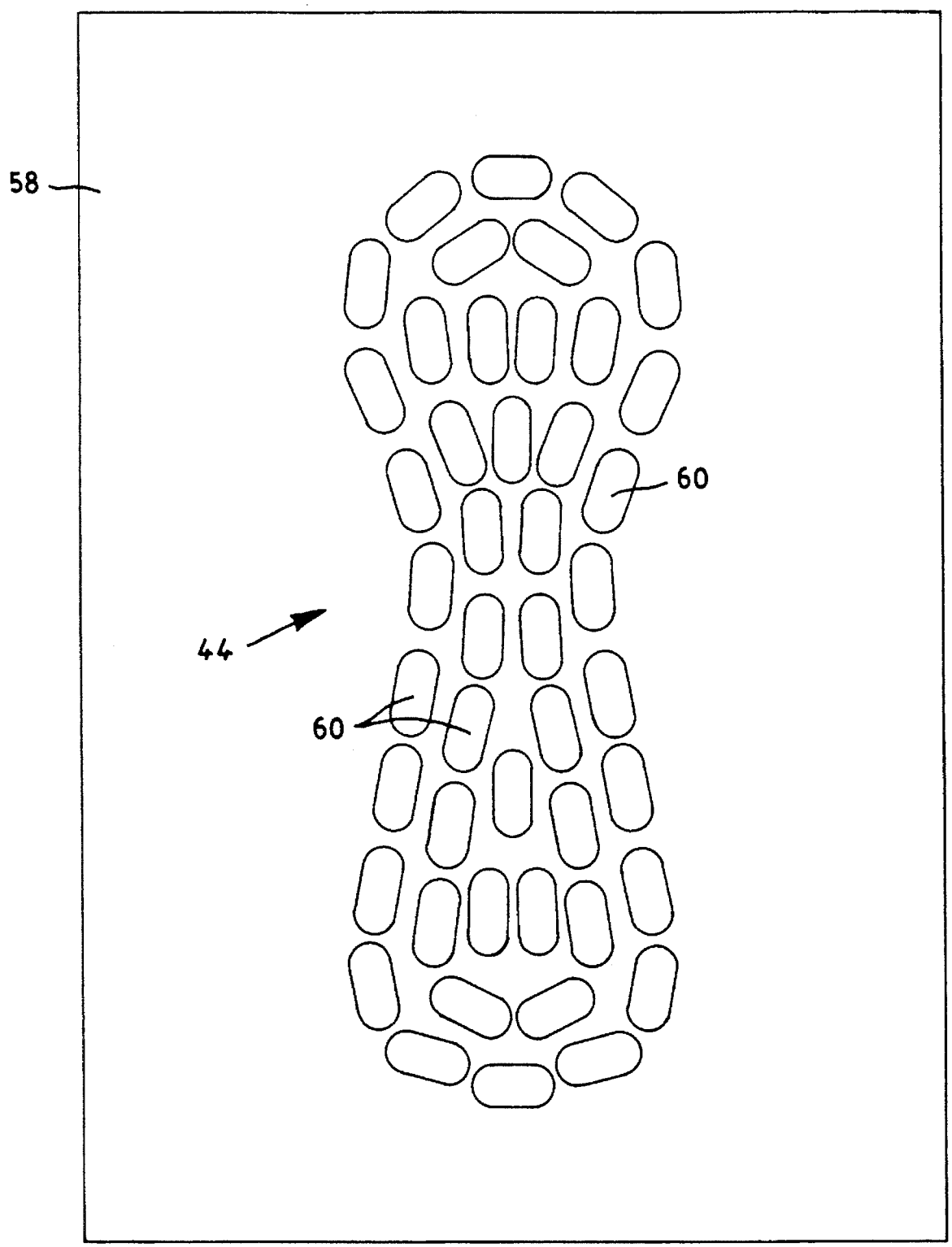
FIG. 7 representatively shows an alternative pattern of openings which can be formed into a screen segment.
Figure 9:
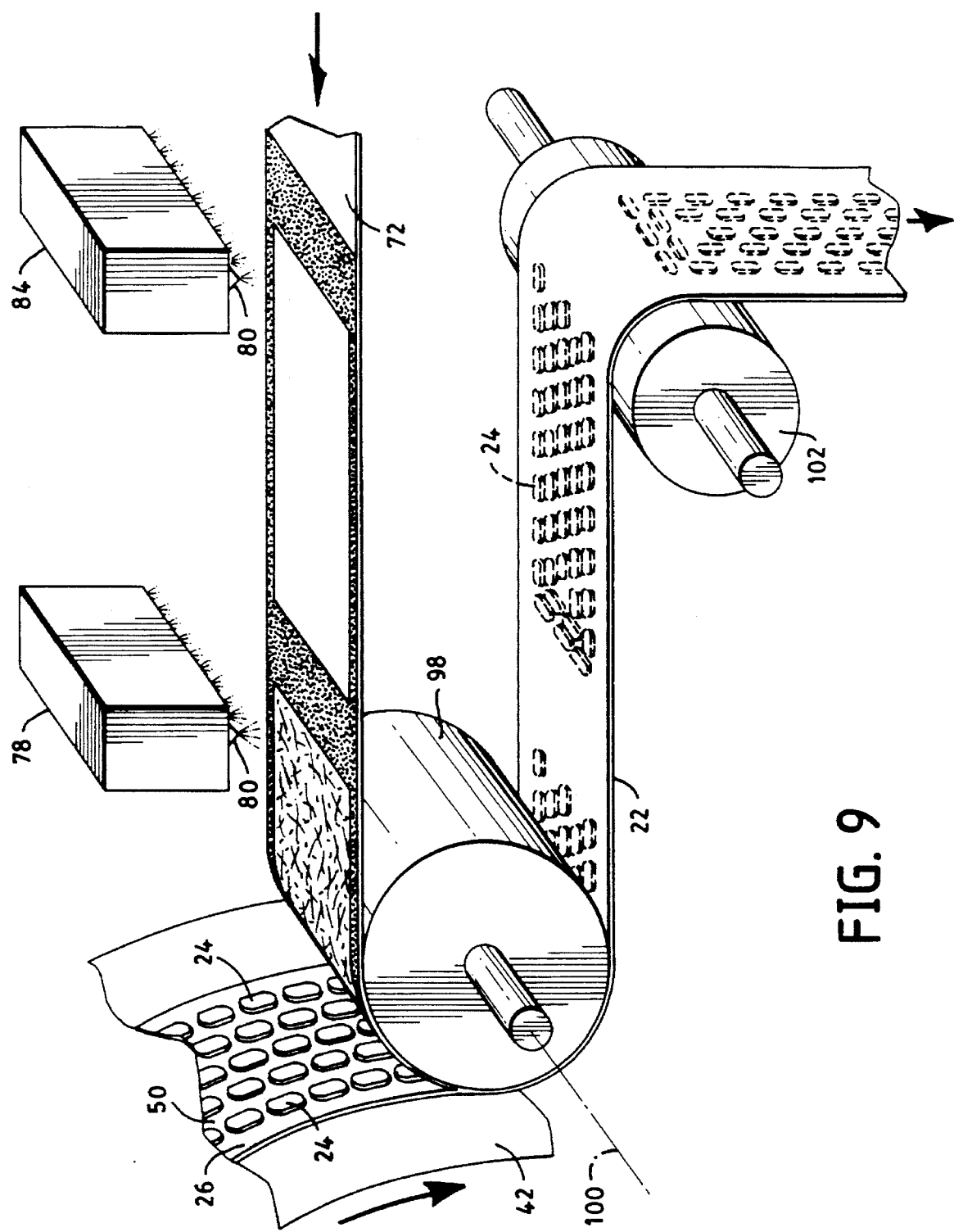
FIG. 9 representatively shows a detail of the section of the invention employed to assemble a covering layer onto the carrier layer.

In the illustrated embodiment, for example, the pattern openings 60 can have an elongate shape with generally parallel side edges and generally semicircular end edges. The individual pattern openings are generally arranged into a system of rows wherein the pattern openings in one row are offset and staggered with respect to the pattern openings located in an immediately adjacent successive row. Alternative configurations of the pattern openings can be arranged with one or more elongate shapes positioned with their relatively longer axes aligned at selected angles which diverge or converge, as desired, toward a longitudinal centerline of the screen segment, as representatively shown in FIG. 7. In general, the arrays for the pattern openings 60 will be constructed to substantially correspond to the desired pattern array of pocket regions 24 (FIG. 8) in composite web 22 (FIG. 9). Various configurations of suitable pocket arrays are described in detail in copending U.S. patent application Ser. No. 145,926 of R. Tanzer et al. filed Oct. 29, 1993 (Attorney Docket No. 10,902), the disclosure of which is hereby incorporated by reference in a manner that is consistent herewith.

A vacuum supplying means, such as provided by conventional vacuum pumps or vacuum fan systems, provides a selected level of relatively low gas pressure at an underside region 64 of the foraminous forming means. In particular, the vacuum supplying means 46 is constructed to provide a desired level of low pressure at the underside region of drum surface 54. The vacuum supplying means is suitably sized and constructed to provide an amount of gas flow through carrier layer 26 and foraminous drum surface 54 at a flow rate and flow volume which is adequate for air-laying the particles of high-absorbency material 28 onto the appointed pocket regions 24 arrayed over the surface of carrier layer 26.

Accordingly, the vacuum supplying means 46 generates suitable levels of vacuum within an appointed vacuum section of forming drum 42, and provides a desired level of vacuum within pattern chamber 30. It should be readily appreciated that the particular levels of vacuum generated within pattern chamber 30 and forming drum 42 will depend upon the individual circumstances of the manufacturing line. For example, at higher rates of rotation of forming drum 42, relatively higher levels of vacuum may be required within pattern chamber 30 and within the vacuum section of forming drum 42. In addition, the use of conveying to transport fibrous or particulate material into the pattern chamber may necessitate the use of higher levels of vacuum. It should also be readily appreciated that the levels of vacuum can also depend upon the porosity of the carrier layer and the particular amount of open area offered by the selected array of pattern openings 60 employed to form the desired pocket regions of high-absorbency material onto the carrier layer.

To improve the effectiveness of the vacuum forming system, blocking means, such as sectional components of sealing material 82, can be selectively located adjacent the lateral sides and/or the longitudinal ends of the predetermined pattern of openings provided on each of the screen segments 58. Suitable sealing materials can be composed of a low porosity material, such as a high density synthetic foam rubber or the like. The sealing material extends radially inward by a distance of at least about 3.5 cm, and is constructed and arranged to block excessive axial and circumferential gas flows in the region of the forming drum which is immediately subjacent the screen segments 58. In the shown embodiment, the sealing material substantially fills the void spaces which are positioned laterally and longitudinally adjacent the screen segments and are located between the drum outer surface 54 and the underside boundary surface 64 of the drum. The sealing material can substantially prevent the intrusion of excessive ambient air under the screen segments, and can help prevent the process gas and gas entrained materials from undesirably bypassing around the pattern of openings. As a result, the gas entrained materials can be more reliably directed onto the desired pocket regions of the carrier layer.

In the illustrated embodiment, for example, the circumferential peripheral length of drum surface 54 which is enclosed at any particular time within pattern chamber 30 has a circumferential length of about 79 cm. The drum surface has an axial length of about 584 cm (about 23 in). When forming drum 42 is rotated to provide a peripheral speed at drum surface 54 of about 124 cm/sec, the level of subatmospheric gas pressure, or relative "vacuum" level, within pattern chamber can be within the range of about 1–8 inches of water, as determined by employing a conventional manometer. With this arrangement, the vacuum within the vacuum section of forming drum 42 is about 10–50 inches of water. When the peripheral speed of drum surface 54 is about 249 cm/sec, the vacuum within pattern chamber 30 can be about 2–7 inches of water, and the vacuum within forming drum 42 can be about 15–40 inches of water. When the peripheral speed of drum surface 54 is about 467 cm/sec, the vacuum within pattern chamber 30 can be about 3–6 inches of water, and the vacuum within forming drum 42 can be about 25–35 inches of water.

In a particular aspect of the invention, the apparatus and method can employ a sweeping means for substantially clearing the particles of high-absorbency material 28 away from the intermediate sections 50 of carrier layer 26 which are located between the desired pocket regions 24 distributed across carrier layer 26. In the illustrated embodiment, for example, the sweeping mechanism can be a pneumatic sweeping mechanism provided by the construction and arrangement of vacuum supplying means 46 and the configuration of exit wall 36 and/or side walls 32.

With reference to FIG. 2, the entrance wall 34 of pattern chamber 30 includes an entrance opening 66 therethrough, and an exit wall 36 includes an exit opening 68 therethrough. The side walls 32 of pattern chamber 30, in a particular aspect of the invention, can be constructed and arranged to be operably sealed against the side wall members of forming drum 42 with a conventional mechanism which substantially blocks the entrance of air while allowing a relatively free, passing movement of the rotating drum. As a result, there is no significant air flow past the side walls 32 into pattern chamber 30. The generated level of vacuum within pattern chamber 30 is sub-atmospheric and produces a quantity of gas flow from the ambient atmosphere into pattern chamber 30 through entrance wall 66. This entrance wall gas flow operably restricts the escape of particulate material from pattern chamber 30 out into the surrounding environment. At the exit region of pattern chamber 30, the pattern chamber vacuum operably generates a quantity and rate of gas flow from the ambient atmosphere into the pattern chamber through exit wall opening 68. By suitably coordinating the level of vacuum within pattern chamber 30 and the movement speed of drum surface 54, the gas flow into pattern chamber 30 can operably sweep away the particles of high-absorbency material 28 away from the intermediate sections 50 of the carrier layer. At the same time, the particulate material 28 located at the appointed pocket regions 24 is substantially left and held in the desired pattern array 44 of pocket regions. As a result, the sweeping means pneumatically clears the high-absorbency material away from the appointed intermediate regions of the carrier layer.

In particular arrangements, for example, the vacuum level within pattern chamber 30 can be at least about 1 inch of water. Alternatively, the pattern chamber vacuum can be at least about 2 inches of water, and optionally, can be at least about 3 inches of water to provide desired performance. In other arrangements, the vacuum level within pattern chamber 30 can be not more than about 8 inches of water. Alternatively, the pattern chamber vacuum can be not more than about 7, and optionally, can be not more than about 6 inches of water to provide desired performance.

In further configurations of the invention, the sweeping means may be provided by other mechanisms. For example, the sweeping means can be provided by brush scarfing, air curtain transvectors or the like.

Another aspect of the invention can include a pattern chamber 30 wherein the side walls 32 of the pattern chamber are not sealed against the sides of the forming drum. This configuration can, for example, be employed when the high-absorbency material is metered and substantially gravity-fed directly into the pattern chamber without utilizing an air-conveying system to deliver the high-absorbency material. In such a configuration, the interior of pattern chamber 30 can be approximately at ambient atmospheric pressure. The vacuum supplying means 46 is configured to provide a vacuum under the foraminous forming surface 54 at a sub-atmospheric pressure level which is sufficient to draw the high-absorbency material and matrix fibers, if any, onto the appointed pocket regions. In addition, the applied vacuum level is sufficient to cause operable airflows which sweep and substantially clear the high-absorbency material and matrix fibers away from the land areas located in between the pocket regions. For example, the vacuum inside the forming drum in the regions under the drum forming surface can be held at a vacuum level which is at least about 10 inches of water. Alternatively the vacuum level can be at least about 15 inches of water, and optionally can be at least about 25 inches of water to provide desired performance. In other configurations, the vacuum inside the forming drum in the regions under the drum forming surface can be held at a vacuum level which is not more than about 50 inches of water. Alternatively the vacuum level can be not more than about 40 inches of water, and optionally can be not more than about 35 inches of water to provide desired benefits. The resultant gravity-fed configuration can form pockets of high-absorbency material while employing patterns of openings 60 that have relatively smaller open areas.

In its various aspects, the present invention can further include a covering means for providing a layer of covering material 72 which sandwiches the pocket regions 24 of high-absorbency material between carrier layer 26 and the covering layer 72 to thereby form a composite laminate web 22, as representatively shown in FIG. 9. The covering means can, for example, comprise a covering material supply roll 70 and a system of transporting rollers and guides 74 (FIG. 1) which are operably configured to deliver the web of covering layer material 72 into a contacting adjacent relation with the composite web 22 composed of carrier layer 26 and the discrete pocket regions of high-absorbency material 28.

Particular aspects of the covering means can further include an attaching means, such as provided by adhesive applicators 78 and/or 80, for securing the covering layer 72 onto carrier layer 26.

In particular aspects of the invention, covering layer 72 is composed of a liquid-permeable web material, such as a liquid-permeable film, tissue, fabric, or the like. The fabric may be woven or nonwoven, and may be composed of a hydrophilic material or composed of a hydrophobic material which has been suitably treated to render it sufficiently hydrophilic. The illustrated embodiment of covering layer 72 is composed of a conventional barrier tissue having a basis weight of about 21.2 gsm and manufactured by a CWP machine process from a furnish composed of 50%/50% Hinton EF (Softwood) and LL-16 Northern Hardwood Kraft (NHWK) fiber. The Hinton EF fiber was obtained from Weldwood, a division of Canada, Ltd., Hinton, Alberta, Canada; and the LL-16 fiber was obtained from Kimberly-Clark Forest Products, Inc., Terrace Bay, Ontario, Canada. The barrier tissue can have a Frazier Porosity of about 80–120 cfm/ft$^2$.

An alternative configuration of the covering layer 72 can, for example, comprise a cellulosic layer of woodpulp fluff. The fluff layer may be substantially unbonded, or optionally, may include a selected proportion of a bonding agent, such as a resin, adhesive, thermally fusible fiber or the like, which is operably distributed therein. For example, a thermally fusible, thermobonding fiber composed of a polyethylene/polypropylene, sheath/core bicomponent fiber may be employed.

The attaching means for securing together carrier layer 26 and covering layer 72 may be constructed to provide any suitable connecting mechanism, such as adhesive bonds, thermal bonds, sonic bonds, stapling, stitching, or the like. The shown embodiment of the attaching means, for example, is configured to provide a predetermined system of adhesive bonds. With reference to FIG. 9, the attaching means can include a pattern adhesive applicator 78, which can comprise an adhesive printing mechanism, adhesive spraying mechanism or the like. The adhesive can be of any suitable type, such as latex adhesive, hotmelt adhesive or the like. For example, suitable adhesive, swirl spraying systems are available from Nordson Corporation, a business having offices in Norcross, Georgia. Other suitable spraying systems are described in U.S. Pat. No. 4,949,668 issued Aug. 21, 1990 to T. Heindel et al. and entitled, SPRAYED ADHESIVE DIAPER CONSTRUCTION, (Attorney docket No. 8357), the disclosure of which is hereby incorporated by reference in a manner that is consistent herewith.

Pattern applicator 78 can be configured to provide an operable distribution pattern of adhesive which bonds covering layer 72 onto carrier layer 26 and sandwiches the discrete pocket regions of high-absorbency material between the carrier and cover layers. In the illustrated embodiment, for example, pattern applicator 78 is constructed to provide a multiplicity of overlapping loops of swirled adhesive to hold together the composite laminate web 22. A plurality of adhesive swirl patterns can be selectively overlapped to provide the desired level of bonding and securement of the high-absorbency material 28 within the appointed pocket regions 24. It should be readily appreciated that other configurations of the pattern adhesive, such as stripes or individual islands of adhesive may be employed to give operable bonding. In addition, it should be readily appreciated that other types of adhesive applicating systems, such as printing, spraying, extrusion, or the like, may be employed to generate the desired arrays of patterned adhesive.

In particular aspects of the invention, pattern applicator 78 can be configured to dispense a substantially water-sensitive adhesive to assemble the composite laminate web 22. The resultant water-sensitive attaching (or attachment) means provides an attachment system wherein the strength of the attachment system is great enough to adequately hold the carrier layer 26 and covering layer 72 together when the system is substantially dry and also when the system is wet. In addition, the wet-strength of the attachment system is configured to be sufficiently low so as to not excessively constrict the swelling expansion of the high absorbency material during the absorption of liquid. The wet-strength of the attachment system is less than the separating force imparted by the swelling of the high absorbency material when the high absorbency material is exposed to aqueous liquids, such as urine. In addition, the water-sensitive attachment system is configured to release at an applied load which is less than the load needed to delaminate the water-sensitive attaching means without excessively tearing the material forming either or both of the carrier layers when such layers are wetted. The water-sensitive attachment system is also configured to release at an applied load which is less than the load needed to excessively burst the material forming either or both of the carrier layers when such layers are wetted. Typically, the applied load is a generally tensile load resulting from the pressure exerted by the expanding high absorbency material when the material absorbs liquid and swells. The appropriate attachment system components, such as layers 26 and 72, are constructed and arranged to be sufficiently strong to withstand this pressure and substantially avoid bursting or tearing.

In other aspects of the invention, the securing strength of the attachment system is greater than zero, and desirably is at least about 0.05 N/cm when the attachment system is wetted. In a particular aspect of the invention, the strength of the attachment system can be arranged to change in response to the presence of the aqueous liquids. More particularly, the attachment strength of the attachment system when it is contacted with an aqueous liquid can be configured to\be less than the attachment strength of the substantially dry attachment system. The relative decrease in the bonding strength of the adhesive can be configured to decrease upon a selected exposure to moisture, thereby providing a desired degree of water-sensitivity.

In the various configurations of the invention, the bonded attached zones of the absorbent laminate 22 are constructed with sufficient integrity to isolate and contain the high absorbency material within each pocket 24. The securement strength between carrier layers 98 and 100 is at least about 0.05 N/cm, peak force, when the absorbent laminate is substantially dry. Alternatively the dry securement strength is at least about 0.08 N/cm, and optionally is at least about 0.1 N/cm to provide desired benefits.

When absorbent laminate 22 is wet, the securement strength between layers 26 and 72 along their inter-attached zones is constructed to be sufficient to maintain the general integrity of the absorbent laminate. In particular aspects of the invention, the wet securement strength is not less than about 0.04 N/cm peak force. Alternatively, the wet securement strength is not less than about 0.07 N/cm, and optionally is not less than about 0.09 N/cm to provide desired benefits.

In desired configurations of the invention, the wet securement strength between carrier layer 26 and covering layer 72 is configured so as to not excessively limit the swelling and expansion of the high absorbency material when the material is absorbing liquids, such as urine. Particular aspects of the invention can be configured so that the wet securement strength between layers 26 and 72 not more than about 5 N/cm, peak force. Alternatively, the wet securement strength is not more than about 2 N/cm, and optionally, is not more than about 1 N/cm to provide desired performance.

For the purposes of the present invention, a suitable technique for determining the dry or wet securement strength of the attaching means is the ASTM Standard Test Method for Peel Resistance of Adhesives ("T-Peel Test); Designation: D 1876–93, approved Jan. 15, 1993.

A detailed description of a suitable water-sensitive attaching means is set forth in U.S. patent application Ser. No. 145,926 of R. Tanzer et al. filed Oct. 29, 1993 (Attorney Docket No. 10,902).

Where the water-sensitive attaching means is provided by a water-sensitive adhesive, the adhesive may, for example, be Cycloflex brand 70-3998 hot-melt adhesive, available from National Starch and Chemical Corporation, a business having offices located in Bridgewater, New Jersey. It is understood that the Cycloflex adhesive is composed of a graft copolymer comprising a vinyl monomer, a polyakkylene oxide polymer and a proportion of polyethylene oxide. Another water-sensitive adhesive is a National Starch 72-4192 water-based adhesive. It is understood that this adhesive is a poly(ethylene-co-vinyl acetate) emulsion stabilized with polyvinyl alcohol.

The attaching system employed in the present invention can further comprise a perimeter attaching means, such as provided by perimeter adhesive applicator 84, which is constructed and arranged to secure the covering layer 72 to carrier layer 26 with a substantially water-insensitive securement. The water-insensitive securement operably holds together the carrier and covering layers even when the layers have become wetted with aqueous liquids, such as urine. A description of an absorbent laminate having substantially water-insensitive securements is described in detail in U.S. patent application Ser. No. 145,925 of R. Tanzer et al. filed Oct. 29, 1993 (Attorney Docket No. 9848) the disclosure of which is hereby incorporated by reference in a manner that is consistent therewith.

The perimeter applicator 84 can include a mechanism for providing a substantially continuous side attachment regions, and a selected pattern of intermittent, longitudinally-spaced, medial attachment regions. Suitable applicator devices are available from Nordson Corporation, a business having offices located at Norcross, Georgia. Where the perimeter attaching means comprises an adhesive applicator, the applicator may be configured to apply the adhesive by employing various conventional techniques, such as printing, extrusion, spraying, or the like. In alternative configurations, the perimeter attaching means may be configured to provide other types of securements, such as sonic bonds, thermal bonds, stitching, sewing, or the like.

As representatively shown in FIGS. 1 and 2, the apparatus and method of the invention can also include a fiber delivery means such as fiberizer 88, for providing a selected quantity of fibrous matrix material 90 into pattern chamber 30 through a suitable conveying system, such as conduit 92. The matrix fibers can advantageously help to maintain a desired distribution of the high-absorbency material 28 within each of the individual pocket regions 24. In particular arrangements, the high-absorbency material can be maintained in a substantially uniform distribution across the area of an individual pocket region, and can help prevent bunching or other segregation of the high-absorbency material within a portion of the pocket region.

In one aspect of the invention, the apparatus is constructed and arranged to provide at least about 80 percent of the pocket regions 24 with a high-absorbency material content of at least about 85 weight percent. In alternative configurations, the invention is constructed to provide a high-absorbency material content of at least about 90 weight percent, and optionally is constructed to provide a high-absorbency material content of at least about 95 weight percent. Desirably, at least about 85%, and more desirably, at least about 90% of the pocket regions 24 contain such weight percentages of high-absorbency material.

In accordance with these aspects of the invention, at least about 80 percent of the discrete pocket regions can contain a matrix fiber content of not more than about 15 weight percent. Alternatively, the matrix fiber content is not more than about 10 weight percent, and alternatively is not more than about 5 weight percent. Desirably, at least about 85%, and more desirably, at least about 90% of the pocket regions 24 contain such weight percentages of matrix fiber material.

The various aspects of the invention can further include a holding means for maintaining the discrete pocket regions of high-absorbency material on carrier layer 26 after the foraminous forming means, such as provided by forming drum 42, has moved the carrier layer 26 out of pattern chamber 30. The illustrated embodiment of the invention incorporates a pneumatic, vacuum-type holding means, but alternative configurations of the invention may employ other holding means, such as an electrostatic holding mechanism or the like.

With reference again to FIG. 2, the primary vacuum section 76 of drum 42 is bounded by radially and axially extending interior walls 136 and 138. An operable pneumatic holding means can be provided by appropriately constructing and arranging the vacuum section 76 to extend through a region 94, which is positioned outside of the region which is underlying and immediately subjacent the pattern chamber 30. Accordingly, a holding section 96 of drum surface 54 is operably provided at a region which is located immediately adjacent to exit opening 68 but outside of the pattern chamber 30. In the shown embodiment, for example, the drum surface holding section 96 has at least a major portion thereof which is located between the chamber exit opening 68 and assembly roller 98. As the composite web 22 is transported through holding section 96 by the rotational movement of the drum surface 54, the amount of vacuum force applied and maintained under holding section 96 operably holds the high-absorbency material 28, along with any matrix fiber material 90, in the desired pocket regions 24 on carrier layer 26. If the holding means is absent, the high-absorbency material may undesirably move away or escape from the desired pocket regions 24 before the assembly and securement of covering layer 72.

As representatively shown in FIG. 9, a substantially continuous web of covering layer material 72 is directed by a suitable mechanism, such as assembly roller 98 which is operably rotatable about its longitudinal axis 100. As covering layer 72 moves around assembly roller 98, the covering layer is brought into laminating contact with carrier layer 26. The adhesive which has been applied to a major facing surface of covering layer 72 by pattern adhesive applicator 78 and/or perimeter adhesive applicator 84 operably adhere together the covering layer 72 and carrier layer 26. The resultant laminating operation sandwiches the predetermined pattern array of pocket regions between the carrier and cover layers. As a result, the pocket regions 24 are substantially held and maintained in a desired pattern array composed of individual segregated pocket regions distributed across the interior of the composite laminate web 22.

In desired aspects of the invention, the assembly roller 98 is constructed with a resilient surface outer cylindrical surface. More particularly the assembly roller outer surface can be constructed with a Shore A-Durometer value of not more than about 60. Alternatively, the Durometer value can be not more than about 45, and optionally can be not more than about 30 to provide desired performance. In other arrangements, the assembly roller outer surface can be constructed with a Durometer value of not less than about 10. Alternatively, the Durometer value can be not less than about 15, and optionally can be not less than about 20 to provide desired benefits. If the surface of assembly roller 98 is too hard, the bonding between carrier layer 26 and covering layer 72 may be poor and the pocket regions 24 may not be adequately maintained. If the assembly roller surface is too soft, the surface may experience excessive wear or overheating, and can again produce poor bonding between the carrier layer and the covering layer.

To help provide a more effective assembling operation, assembly roller 98 can be urged against covering web 72 with a resilient pressuring means, such as a pneumatic actuator 86. In particular aspects of the invention the pressuring means can be constructed to provide an assembly pressure level of not less than about 5 psi. Alternatively, the assembly pressure can be not less than about 10 psi, and optionally, can be not less than about 15 psi to provide improved performance. In other aspects, the pressuring means can be constructed to provide an assembly pressure level of not more than about 300 psi. Alternatively, the assembly pressure can be not more than about 175 psi, and optionally can be not more than about 50 psi to provide desired benefits. If the pressure is too low, insufficient bonding may occur, and if the pressure is too high, the pocket regions or the high absorbency material may become excessively distorted or crushed.

After the assembling operation has formed the composite laminate web 22, the laminate web is operably removed from the surface of forming drum 42 and directed to other areas of the apparatus for further processing. A stripper roll 102 can be employed to help separate the composite laminate web 22 from the drum surface 54.

Various aspects of the invention can include a disposing means for placing at least one body of distribution material, such as distribution layer 104, adjacent to composite web 22. In the illustrated embodiment of the invention, a disposing means, such as provided by for pad forming chamber 106 and associated assembling components, are configured to place distribution layer 104 adjacent to the composite laminate web 22.

With reference to FIG. 1, the disposing means can include a second pad forming chamber 106 for producing at least one web of a fibrous distribution material, and a second fiber delivering means, such as hammermill fiberizer 108, for supplying discrete separated fibers of distribution material into pad forming chamber 106. A foraminous transporting means, such as pad forming drum 110 moves the at least one web of distribution material 104 out from the pad forming chamber 106. A conveying means, such as a system of transporting belts and rollers 124, 126, and 128, move the web of distribution material 104 into a selected adjacent position relative to the composite web, such as provided for by composite laminate 22.

In the representatively shown configuration of the invention, for example, a conventional hammermill type of fiberizer disintegrates wood pulp sheets into a multiplicity of individual wood pulp, fluff fibers. The wood pulp fibers are delivered into pad forming chamber 106 for deposition onto an outer peripheral, foraminous forming surface of pad forming drum 110. Pad forming drum 110 is a conventional forming drum, such as described in detail in U.S. Pat. No. 4,666,647 issued May 19, 1987 to K. Enloe et al. (Attorney Docket No. 6900). Techniques for configuring the peripheral foraminous forming surface of pad forming drum 110 are described in detail in U.S. Pat. No. 4,761,258 issued Aug. 2, 1988 to K. Enloe (Attorney Docket No. 6999). A suitable vacuum system (not shown) generates a low pressure region within the pad forming drum to operably draw the wood pulp fibers onto the drum forming surface to produce distribution layer 104. The pad forming drum 110 can be appropriately configured to provide pad zones which have a relatively higher basis weight compared to other sections of the distribution layer.

The illustrated pad forming system can include a mechanism for providing a web of forming tissue 112 onto the peripheral foraminous forming surface of pad drum 110. As a result, the wood pulp fibers within pad chamber 106 are deposited onto forming tissue 112. The forming tissue is sufficiently porous to allow air flows therethrough which are adequate for depositing the desired basis weights of wood pulp fluff fibers onto the forming tissue to produce the desired configurations of distribution layer 104.

As the forming tissue and associated wood pulp fluff fibers are moved out from pad chamber 106, a web of barrier tissue 114 is brought into contact therewith to operably form a sandwich structure in which pads of wood pulp fibers are held between forming tissue 112 and barrier tissue 114. The resulting distribution layer laminate 104 can then be passed into a compressing means, such as provided by the nip between a pair of debulking rollers 116, to compact the distribution layer 104 and increase a density thereof. An assembly attaching means, such as provided by assembly adhesive applicator 118, provides for a selective securement of the composite laminate web 22 to the web of distribution material 104. In the shown embodiment, for example, distribution layer 104 and composite laminate 22 are passed into the nip region of a pair of assembly rollers 120 to operably interconnect the distribution layer and composite laminate web to form a composite absorbent web 122.

In an alternative aspect of the invention representatively shown in FIG. 1, the pad forming system comprising chamber 106 and forming drum 110 can be configured to produce a distribution layer which is composed of woodpulp fluff and provides the form and function of a modified covering web layer 172. The distribution layer can optionally include a predetermined amount of high-absorbency material, such as superabsorbent polymer material. In the shown embodiment, for example the modified covering web can be directed by guiding means, such as a system of rollers including rollers 140, along a web path which extends past adhesive applicators 78 and 84, and around assembly roller 98. Accordingly, the assembly roller can nip the modified covering web 172 against the carrier layer 26 and the pocket regions of high-absorbency material laid thereon.

The various aspects of the invention can also include a regulating means for controlling a tension applied to carrier layer 26 to control a porosity of the carrier layer within pattern chamber 30. As representatively shown in FIG. 1, the tension regulating means can include a conventional dancer roll assembly 62, and can include a tension, feedback control unwind mechanism, such as available from Martin Automatic, Inc., a business having offices in Rockford, Illinois. The control of the tension applied to carrier layer 26 can, for example, be accomplished by means of an air pressure applied to the dancer roll.

Figure 10:
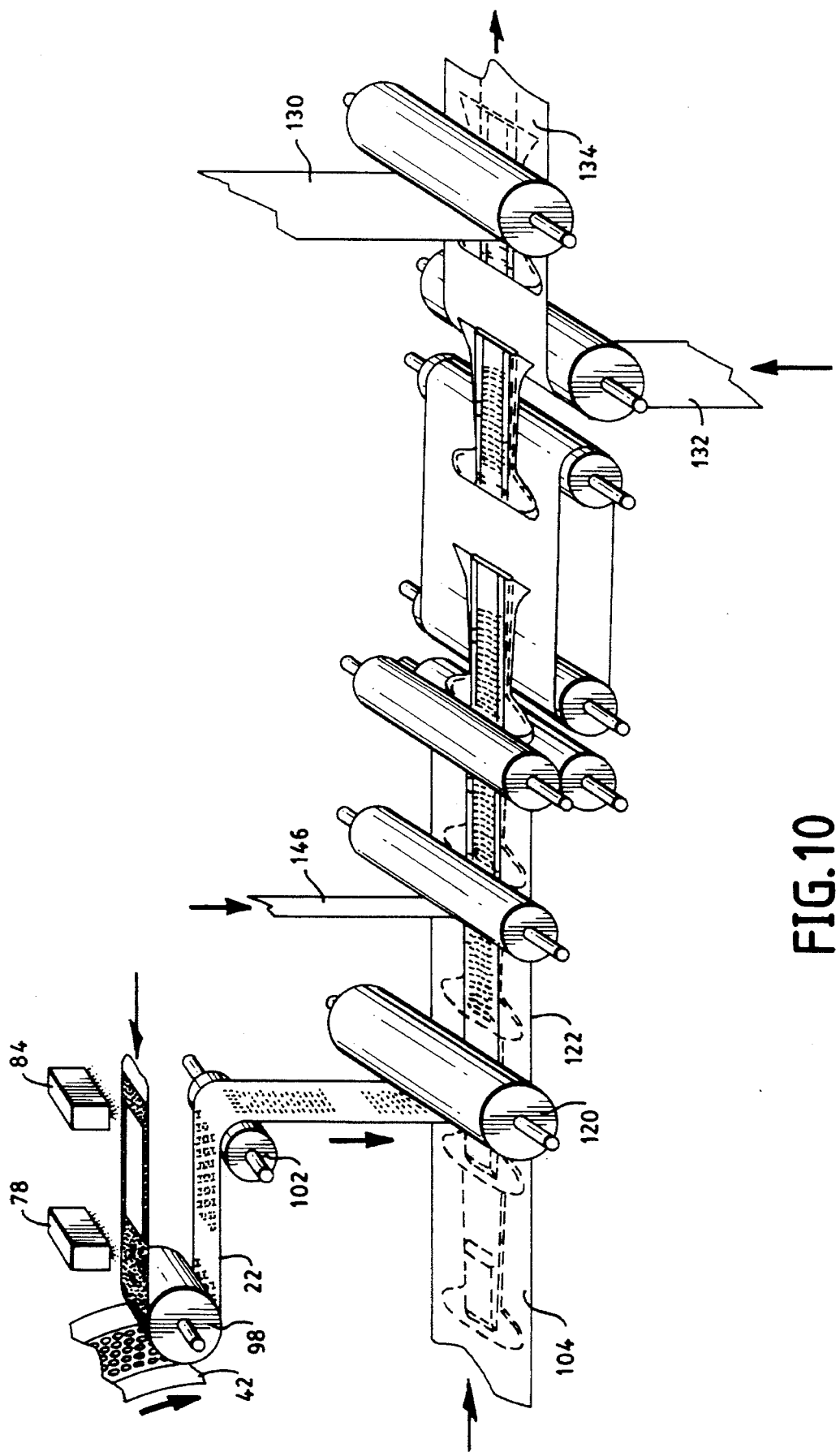
FIG. 10 representatively shows a composite web being assembled with other components of an absorbent article.
Figure 11:
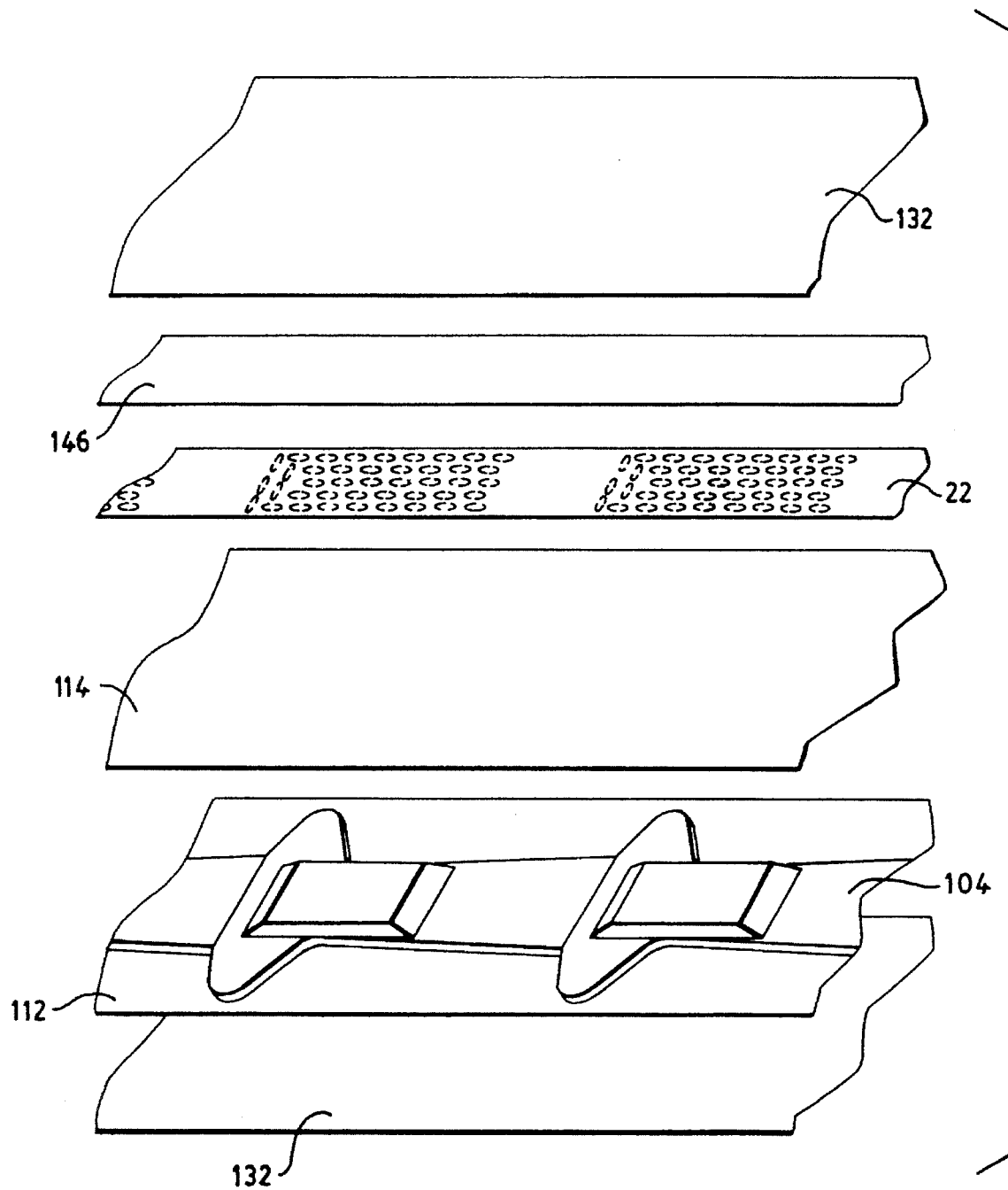
FIG. 11 representatively shows a exploded view of a web assembly composed of an interconnected plurality of appointed articles which can be produced with the present invention.

With reference to FIGS. 10 and 11, composite absorbent web 122 and other desired components, such as a web of surge management material 146, can be sandwiched between a topsheet web 130 and a backsheet web 132 to operably produce an article web 134. It should be readily appreciated that conventional mechanisms may be employed to assemble the other desired components of the end article onto article web 134. Eventually, the article web is divided into individual articles employing conventional techniques.

Having described the invention in rather full detail, it will be readily apparent that various changes and modifications can be made without departing from the spirit of the invention. All of such changes and modifications are contemplated as being within the scope of the invention, as defined by the subjoined claims.

We claim:

1. An apparatus for forming a composite web having a selected plurality of discrete pocket regions which are distributed on a carrier layer and contain high-absorbency material, said apparatus comprising:

a pattern chamber;

particulate supplying means for providing particles of high-absorbency material into said pattern chamber;

web supplying means for providing a gas permeable carrier layer; foraminous forming means for moving said carrier layer through said pattern chamber, said forming means including a pattern of openings which are formed therethrough and are arranged to provide for a selected pattern of said discrete pocket regions;

vacuum supplying means for providing a selected level of relatively low gas pressure at an underside region of said forming means to produce a selected gas-flow through said carrier layer and said foraminous forming means to form said pocket regions;

covering means for providing a layer of liquid-permeable covering material to sandwich said pocket regions of high-absorbency material between said carrier layer and said covering layer.

2. An apparatus as recited in claim 1, further comprising a holding means for maintaining said discrete pocket regions of high-absorbency material on said carrier layer after said forming means has moved said carrier layer out of said pattern chamber.

3. An apparatus as recited in claim 2, further comprising sweeping means for substantially clearing said high-absorbency material from intermediate sections of said carrier layer which are located between said selected pocket regions on said carrier layer.

4. An apparatus as recited in claim 3, further comprising fiber delivering means for providing a selected quantity of fibrous matrix material into said pattern chamber; and wherein said apparatus is constructed to provide at least about 80% of said discrete pocket regions with a high-absorbency material content of at least about 85 wt %.

5. An apparatus as recited in claim 4, further comprising an attaching means for securing said covering layer to said carrier layer.

6. An apparatus as recited in claim 5, wherein said attaching means includes a perimeter attaching means for securing said covering layer to said carrier layer with a substantially water-sensitive securement.

7. An apparatus as recited in claim 6, wherein said attaching means includes a pattern attaching means for securing said covering layer to said carrier layer with a substantially water-insensitive securement.

8. An apparatus as recited in claim 1, further comprising sweeping means for pneumatically clearing said intermediate sections of said carrier layer.

9. An apparatus as recited in claim 1, further comprising disposing means for placing at least one body of distribution material adjacent to said composite web.

10. An apparatus as recited in claim 9, wherein said disposing means comprises:
- a second forming chamber for producing at least one web of fibrous distribution material;
- a second fiber delivering means for supplying discrete separated fibers of distribution material into said second forming chamber; foraminous transporting means for moving said at least one web of distribution material out from said second forming chamber; conveying means for moving said at least one web of distribution material into a selected adjacent position relative to said composite web.

11. An apparatus for forming a composite web having selected discrete pocket regions which are distributed on a carrier layer and contain high-absorbency material, said apparatus comprising:
- a pattern chamber having opposed side walls, an entrance end wall and an exit end wall;
- particulate supplying means for providing particles of high-absorbency material into said pattern chamber;
- web supplying means for providing a gas permeable carrier layer;
- foraminous forming means for moving said carrier layer through said pattern chamber, said forming means including a pattern of openings which are formed therethrough and are arranged to provide for a selected pattern of said discrete pocket regions;
- vacuum supplying means for providing a selected level of relatively low gas pressure at an underside region of said forming means to produce a selected gas-flow through said carrier layer and said foraminous forming means which directs said high-absorbency material to said pocket regions; and
- regulating means for controlling a tension applied to said carrier layer to control a porosity of said carrier layer within said pattern chamber.

12. A method for forming a composite web having a selected plurality of discrete pocket regions which are distributed on a carrier layer and contain high-absorbency material, said method comprising the steps of:
- (a) providing particles of high-absorbency material into a pattern chamber;
- (b) providing a gas permeable carrier layer;
- (c) moving said carrier layer through said pattern chamber with a foraminous forming means having a pattern of openings which are formed therethrough and are arranged to provide for a selected pattern of said discrete pocket regions;
- (d) supplying a selected level of relatively low gas pressure at an underside region of said forming means to produce a selected airflow through said carrier layer and said foraminous forming means to form said pocket regions;
- (e) providing a layer of covering material which sandwiches said regions of high-absorbency material between said carrier layer and said covering layer.

13. A method as recited in claim 12, further comprising the step of (f) holding said discrete pocket regions of high-absorbency material on said carrier layer after said forming means has moved said carrier layer out of said pattern chamber.

14. A method as recited in claim 13, further comprising the step of (g) substantially clearing said high-absorbency material from intermediate sections of said carrier layer which are located between said selected pocket regions.

15. A method as recited in claim 14, further comprising the steps of:
- (h) delivering a selected quantity of fibrous matrix material into said pattern chamber; and
- (i) providing at least about 80% of said discrete pocket regions with a high-absorbency material content of at least about 85 wt %.

16. A method as recited in claim 15, further comprising the step of (j) securing said covering layer to said carrier layer.

17. A method as recited in claim 16, wherein said securing step (j) includes the step of securing said covering layer to said carrier layer with a substantially water-sensitive securement.

18. A method as recited in claim 17, wherein said securing step (j) includes the step of securing said covering layer to said carrier layer with a substantially water-insensitive securement.

19. A method as recited in claim 14, wherein said clearing step (g) pneumatically clears said intermediate sections of the carrier layer.

20. A method as recited in claim 12, further comprising the step of (k) placing at least one body of substantially hydrophilic distribution material adjacent to said composite web.

21. A method as recited in claim 20, wherein said placing step (k) comprises the steps of:
- providing a second forming chamber for producing at least one web of fibrous distribution material;
- supplying discrete separated fibers of distribution material into said second forming chamber;
- moving said at least one web of distribution material out from said second forming chamber;
- conveying said at least one web of distribution material into a selected adjacent position relative to said composite web.

22. A method for forming a composite web having selected discrete pocket regions which are distributed on a carrier layer and contain high-absorbency material, said method comprising the steps of:
- (a) providing particles of high-absorbency material into a pattern chamber;
- (b) providing a gas permeable carrier layer;
- (c) moving said carrier layer through said pattern chamber with a foraminous forming means having a pattern of openings which are formed therethrough and are arranged to provide for a selected pattern of said discrete pocket regions of high-absorbency material;
- (d) supplying a selected level of relatively low gas pressure at an underside region of said forming means to produce a selected airflow through said carrier layer and said foraminous forming means which directs said high-absorbency material to said pocket regions; and
- (e) regulating a tension applied to said carrier layer to control a porosity of said carrier layer within said pattern chamber.

* * * * *